United States Patent [19]

Sheth et al.

[11] 4,126,672

[45] Nov. 21, 1978

[54] SUSTAINED RELEASE PHARMACEUTICAL CAPSULES

[75] Inventors: Prabhakar R. Sheth, Pearl River, N.Y.; Jacques L. Tossounian, Pine Brook, N.J.

[73] Assignee: Hoffmann-La Roche Inc., Nutley, N.J.

[21] Appl. No.: 834,347

[22] Filed: Sep. 19, 1977

Related U.S. Application Data

[60] Continuation-in-part of Ser. No. 655,302, Feb. 4, 1976, abandoned, which is a division of Ser. No. 559,107, Mar. 17, 1975, abandoned.

[51] Int. Cl.² .......................... A61K 9/52; A61K 9/26
[52] U.S. Cl. ............................................. 424/22; 424/19
[58] Field of Search ..................................... 424/19–22

[56] References Cited

U.S. PATENT DOCUMENTS

| | | | |
|---|---|---|---|
| 3,065,143 | 11/1962 | Christenson et al. | 424/22 |
| 3,122,474 | 2/1964 | Carstensen | 424/244 |
| 3,140,978 | 7/1964 | Zentner | 424/260 |
| 3,365,365 | 1/1968 | Butler et al. | 424/20 |
| 3,418,999 | 12/1968 | Davis | 424/14 X |
| 3,427,378 | 2/1969 | Henderson et al. | 424/14 |
| 3,444,290 | 5/1969 | Wai | 424/4 |
| 3,449,489 | 6/1969 | Gaunt | 424/32 X |
| 3,555,151 | 1/1971 | Kaplan et al. | 424/156 |
| 3,574,820 | 4/1971 | Johnson et al. | 424/22 |

FOREIGN PATENT DOCUMENTS 623,704 4/1963 Belgium.
2,002,816 7/1970 Fed. Rep. of Germany.

OTHER PUBLICATIONS

C.A. 60 #10484g(1964), 73 #69844c(1970), 76 #121938q(1972), 81 #54444p(1974).

*Primary Examiner*—Shep K. Rose
*Attorney, Agent, or Firm*—Jon S. Sax; Bernard S. Leon; R. Hain Swope

[57] ABSTRACT

Sustained release pharmaceutical capsules suitable for oral administration and particularly suitable for sustained release therapy with certain benzodiazepines, e.g. chlordiazepoxide and diazepam, are disclosed. The formulation contained in the disclosed capsules is hydrodynamically balanced to be buoyant in gastric fluid thereby remaining buoyant in the gastric fluid until substantially all of the medicament therein has been released.

4 Claims, No Drawings

SUSTAINED RELEASE PHARMACEUTICAL CAPSULES

RELATED APPLICATIONS

This application is a continuation-in-part of U.S. patent application Ser. No. 655,302, filed Feb. 4, 1976 now abandoned which in turn is a divisional application of U.S. patent application Ser. No. 559,107, filed Mar. 17, 1975, now abandoned.

BACKGROUND OF THE INVENTION

The convenience of administering a single dose of medication which releases active ingredient over an extended period of time as opposed to the administration of a number of single doses at regular intervals has long been recognized in the pharmaceutical art. The advantage to the patient and clinician in having consistent and uniform blood levels of medication over an extended period of time are likewise recognized. In most sustained release preparations known to the pharmaceutical art, medicinal agents are either coated with varying thicknesses of some type of relatively insoluble material or are imbedded into a rigid lattice of resinous material. In such preparations, the object is to continuously provide drug for absorption into the blood stream to replace the amount eliminated while the dosage form is passing through the gastrointestinal tract of the patient.

The conventional approaches to sustained release formulation briefly outlined above can be disadvantageous in that certain classes of active ingredients are not suited to absorption during passage through the gastrointestinal tract due to their physiochemical properties and/or favorable sites of absorption. For example, most acidic medicaments are principally absorbed from the stomach whereas most basic medicaments are absorbed primarily from the intestines. Most medicaments will undergo varying degrees of change in solubility by passage from the acutely acidic conditions of the stomach to the neutral to alkaline conditions of the intestines. For example, ferrous salts are more soluble in the stomach than in the intestines. Finally, there are medicaments, e.g. antacids, which are intended to act in the stomach and therefore lose most beneficial properties when they pass into the intestines.

It is readily apparent in view of the above considerations that a large number of medicaments are not amenable to conventional sustained release formulations which are not retained in the stomach and which release medicament in the intestines. It is equally apparent that a sustained release formulation which is retained in the stomach and which slowly releases medicament over an extended period of time would be eminently suited to such medicaments. Such a sustained release formulation is provided by the present invention.

The principle of sustained release which characterizes the formulations contained in the capsules of the subject invention is unique in the art, i.e. the formulation remains buoyant and freely floating in the gastric fluid for an extended period of time during which substantially all of the medicament contained therein is released into the gastric fluid for absorption. Although many mechanisms of sustained release are recognized in the art and the concept of a floating tablet is known, there is no teaching in the art of a formulation which remains intact and buoyant in the gastric fluid while substantially all of the medicament is released therefrom.

BRIEF DESCRIPTION OF THE INVENTION

Formulations suitable for the preparation of sustained release capsules suitable for oral administration are provided. The formulations comprise one or more medicaments in combination with a hydrocolloid or mixtures of hydrocolloids so as to be hydrodynamically balanced so that, in contact with gastric fluid, they have a bulk density (specific gravity) less than one and therefore are buoyant in gastric fluid and thus are retained in a buoyant state in the stomach until substantially all the medicament is released therefrom.

DETAILED DESCRIPTION OF THE INVENTION

In accordance with the present invention, formulations for the preparations of sustained release capsules for oral administration are provided which are hydrodynamically balanced to have a bulk density (specific gravity) of less than one in contact with gastric fluid and which therefore will remain floating in gastric fluid which has a specific gravity of between 1.004 and 1.010. The sustained release formulations of the present invention comprise a homogeneous mixture of one or more medicaments with one or more hydrophillic hydrocolloids which, upon dissolution of the capsule and contact of the formulation with the gastric fluid, will form on the surface thereof a soft gelatinous mass, thus causing it to enlarge somewhat and acquire a bulk density (specific gravity) of less than one. The medicament is slowly released from the surface of the gelatinous mass which, due to its buoyancy, remains buoyant in the gastric fluid. Ultimately, after substantially all of the medicaments therein are released, the gelatinous mass disperses.

Upon oral ingestion of the sustained release capsules of the present invention, the capsule shell dissolves leaving the formulation in contact with gastric fluid. Upon contact with gastric fluid, the outermost hydrophillic colloid hydrates to form an outside barrier which substantially retains the shape of the capsule and therefore acts to prevent the mass from disintegrating. The hydrated layer thereafter slowly dissolves releasing medicament. There is also a release of medicament by leaching action at or near the surface of the mass. As new surface is exposed to gastric fluid it becomes hydrated, thus maintaining the integrity of the barrier. This process is continuously repeated until the medicament is substantially leached out. Thereafter the remaining matrix which is still buoyant in gastric fluid slowly dissolves and is eliminated. It has been found that the release pattern and resulting blood levels attained with the sustained release formulation of the invention has advantages over other sustained release mechanisms known in the art. Moreover, it has been found that the sustained release formulation of the present invention unexpectedly produces optimum blood levels with certain medicaments, particularly the benzodiazepines such as chlordiazepoxide and diazepam. The results with chlordiazepoxide are considered to be particularly surprising in that the blood levels obtained with the sustained formulations of the present invention were clearly superior to blood level obtained after oral administration of chlordiazepoxide in sustained release preparations known in the pharmaceutical arts. In fact, all known sustained release mechanisms previously tested with chlordiazepoxide failed to produce satisfactory blood levels. Similar results were noted with diazepam.

Hydrocolloids suitable for use in the sustained release formulations of the subject invention include one or more natural, partially or totally synthetic anionic or, preferably, nonionic hydrophillic gums, modified cellulosic substances or proteinaceous substances such as, for example, acacia, gum tragacanth, locust bean gum, guar gum, karaya gum, agar, pectin, carrageen, soluble and insoluble alginates, methylcellulose, hydroxypropylmethylcellulose, hydroxypropylcellulose, hydroxyethylcellulose, sodiumcarboxymethylcellulose, carboxypolymethylene (Carbopol-Cabot Corporation), gelatin, casein, zein, bentonite, Veegum (R. T. Vanderbilt Co.) and the like. A preferred hydrocolloid in accordance with the present invention is hydroxypropylmethylcellulose. The use of such materials in pharmaceutical compounding is recognized in the art. For example, Kaplan et. al. U.S. Pat. No. 3,555,151 discloses the use of such hydrocolloids in sustained release antacid preparations.

In order to successful practice the present invention the hydrocolloids utilized must hydrate in acidic medium, i.e., gastric fluid with a pH equivalent to 0.1N hydrochloric acid, i.e., a pH of approximately 1.2. Furthermore, although the initial bulk density of the formulation contained in the sustained release capsules of the invention may initially be greater than one, it is essential that the formulation be hydrodynamically balanced to have a bulk density of less than one when in contact with gastric fluids to assure buoyancy. There are a number of methods whereby the rate of release of medication from the sustained release formulation of the present invention can be adjusted. First, the choice of a particular hydrocolloid or mixture of hydrocolloids can affect the release rate, e.g., high viscosity hydrocolloids, e.g., hydroxypropyl methylcellulose, 4000 cps, hydrate more slowly and maintain a soft mass for a longer time than low viscosity hydrocolloids, e.g., hydroxypropyl methylcellulose, 10 cps. Further, edible, pharmaceutically inert, fatty materials having a specific gravity of less than one can be added to the formulation to decrease the hydrophillic property of the formulation and therefore increase buoyancy. Examples of such materials include: a purified grade of beeswax; fatty acids; long chain fatty alcohols such as, for example, cetyl alcohol, myristyl alcohol, stearyl alcohol; glycerides such as glyceryl esters of fatty acids such as, for example, glyceryl monostearate, glyceryl distearate, glyceryl esters of hydrogenated castor oil and the like; or oils such as mineral oil and the like or acetylated glycerides.

There may also be incorporated into the sustained release formulation of the present invention additional edible non-toxic ingredients recognized in the art of pharmaceutical compounding such as excipients, preservatives, stabilizers, tabletting lubricants and the like. The choice of such materials and the amounts to be utilized are considered to be within the purview of one skilled in the art. It is to be borne in mind, however, that such conventional pharmaceutical adjuncts which might adversely affect the hydrodynamic balance of the sustained release formulation of the present invention are not suitable for use therein.

The amount of the active medicament or mixtures thereof in the sustained release formulation of the present invention can vary over a wide range, i.e., from about 0.1% by weight to about 90% by weight. The amount of active substances present is usually between about 5% by weight and 50% by weight. Factors which govern the amount of active substance present in the sustained release formulations of the present invention are, for example, the amount required to give full therapeutic dosage, the bulk density thereof, the hydrophillic or hydrophobic properties thereof, the stability thereof and the like. These properties are known or are easily ascertainable by a person skilled in the art and the formulation adjustments required to incorporate any given therapeutically active substance into a sustained release formulation in accordance with the present invention are considered to be within the purview of the art. The amount of hydrocolloid ingredient present in the sustained release formulation of the present invention may also vary within a wide range, i.e., from about 5% by weight to about 99.9% by weight. Again, the amount of hydrocolloid ingredient to be utilized will vary in relation to the amounts and properties of the active ingredient and inert pharmaceutical adjuncts utilized. Generally, the amount of hydrocolloid present will be between about 20% by weight and about 75% by weight.

Wherein one or a mixture of fatty materials is present in the sustained release formulations of the invention, such material comprises up to about 60% by weight of the total formulation. In general, wherein the formulations do contain a fatty material, such material is present in from about 5% by weight to about 30% by weight. The amount of fatty material utilized is governed by the amounts and physical characteristics of both the active ingredient and the hydrocolloid with the object being to achieve a hydrodynamically balanced formulation, i.e., a formulation which acquires a bulk density (specific gravity) of less than one in gastric fluids.

The amount of edible, inert pharmaceutical adjunct materials which may be present in the sustained release formulations of the present invention will also vary in accordance with the amounts and physical properties of the other ingredients. Such materials which themselves have a bulk density of less than one, e.g. ethylcellulose will enhance the buoyancy of the formulation. More importantly, it is possible to utilize the selection of inert pharmaceutical adjunct materials to modify the rate of release of the formulation. For example, soluble excipients, e.g., lactose, mannitol and the like, will increase the rate of release whereas insoluble excipients e.g., dicalcium phosphate, terra alba and the like, will decrease solubility. Wherein such pharmaceutical adjunct materials are included in the formulations of the invention, they can be present in up to 80% by weight of the final formulation. Generally, such conventional pharmaceutical adjuncts are present in from about 5% by weight to about 60% by weight of the formulation. The inclusion of and choice of such materials is again considered to be within the purview of the art utilizing the principles of the present invention.

The hydrodynamically balanced sustained release formulations of the present invention are prepared by techniques well established in the art. In most instances, all that is required is the thorough mixing of all ingredients to form a homogeneous mixture and milling or comminuting the mixture to a relatively fine particle size, i.e. all particles passing a 100 mesh screen. Milling the mixture to a very fine particle size does not detract from the sustained release mechanism and in fact exerts a positive effect thereon. Under certain circumstances the conventional pharmaceutical techniques of slugging, wet granulating or extruding may be required to achieve proper fill weight in the capsule. It is preferred, however, to comminute the mixture to a fine particle size and completely fill the capsule therewith. Of the pharmaceutical capsules known to the art, hard gelatin capsules are preferred. The capsules should be completely filled. Adjustments in the formulation necessary to achieve a complete fill are considered to be within the skill of the art within the guidelines set forth herein.

The medicament or combination of medicaments which are amenable to sustained release therapy utilizing the novel formulations of the present invention include any of those suitable for oral administration. It is to be understood that the present invention is not to be construed as being limited to any particular medicament or class of medicaments. Further, the sustained release formulation of the present invention is not restricted to medicaments which are principally absorbed from the stomach since it has been found that it is equally efficacious with medicaments which are absorbed from the intestines, e.g., chlorpheniramine maleate. The sustained release dosage formulation of the invention could obviously not be utilized with medicaments which are acid sensitive. Among the various classes of medicaments which can be advantageously administered via a sustained release dosage form are, for example, antibiotics, e.g., the penicillins, cephalosporins and tetracyclines; catecholamines, e.g., epinephrine and the amphetamines; analgesics, e.g., aspirin; sedatives, e.g., the barbiturates, anticonvulsants, antinauseants, muscle relaxants, hypotensives, the vitamins and the like. It is reported in the literature that the irritation of the stomach caused by aspirin is the result of contact of this very acidic substances with the stomach walls. Therefore, it will be appreciated that the formulations of the invention are particularly advantageous for the administration of aspirin since they remain buoyant in gastric fluid.

A class of medicaments to which the sustained release formulation of the subject invention is particularly amenable is the benzodiazepines, e.g., chlordiazepoxide, diazepam, oxazepam, bromazepam and the like. It is noteworthy that, after a number of sustained release mechanisms known to the art proved unsuccessful, superior results were obtained with chlordiazepoxide utilizing the formulations of the subject invention.

The sustained release formulations of the present invention are also particularly amenable to the administration of medicaments which are only absorbed through the stomach or upper portion of the intestines, e.g., ferrous salts such as ferrous fumarate, or which exert a therapeutic effect in the stomach, for example, antacids such as the oxides, hydroxides and carbonates of magnesium aluminum hydroxide, magnesium trisilicate and the like. Wherein such substances generate carbon dioxide, bubbles will become entrapped by the hydrated outer layer of the formulation thus enhancing the buoyancy thereof. This phenomenon can likewise be utilized to enhance the buoyancy of non-antacid containing formulation, i.e. the inclusion of small amounts of carbon dioxide generating bases therein.

The sustained release formulation of the present invention has been found to remain buoyant in gastric fluid despite the presence of surfactants or food. Likewise, the continual release of medicament and therefore the blood levels thereof has been found to be unaffected by the presence of surfactants or foods. The efficacy of medicaments administered utilizing the sustained release formulation of the present invention has been found to be independent of the site of absorption of the particular medicament. Utilizing dogs which had ingested capsules prepared in accordance with the invention containing barium sulfate, it has been demonstrated by the use of x-ray techniques that such capsules remain buoyant in the gastric fluid and do not adhere to the walls of the stomach.

The following examples further illustrate the invention.

EXAMPLE 1

Sustained release capsules containing chlordiazepoxide were prepared as follows:

| Ingredient | Mg/capsule |
|---|---|
| Chlordiazepoxide | 30.6 |
| Hydroxypropylmethylcellulose, 4000 cps | 100.4 |
| Lactose Anhydrous | 30.0 |
| Sterotex K* | 58.0 |
| Talc | 50.0 |
| Magnesium Stearate | 6.0 |
| Total | 275.0 |

*A hydrogenated cottonseed oil manufactured by Capital City Products, Columbus, Ohio.

The chlordiazepoxide, methylcellulose and lactose were homogeneously blended in a suitable blender after which the mixture was passed through a Fitzpatrick Comminuting Machine at high speed utilizing a No. 2B screen with knives forward. The Sterotex K, talc and magnesium stearate were then added to the mixture and the whole blended for an additional 5 minutes. The mixture was then passed through a Fitzpatrick Comminuting Machine at high speed utilizing a No. 0 plate, knives forward. The mixture, after it passes tne No. 0 plate on the Fitzpatrick Comminuting Machine is of sufficiently fine particle size that 100% will pass a 100 mesh screen. The blending and milling procedures were repeated so that not less than 50% of the mixture passed a 200 mesh screen. The mixture was filled into No. 2 size pink opaque capsules.

The thus-formed capsules were tested for in vitro release rates by the rotating bottle technique in simulated gastric fluid. The results of these tests are set forth in Table I.

TABLE I

| Percent of Active Ingredient Released | |
|---|---|
| Time (hours) | Gastric Fluid (pH 1.2) |
| 0 | 0 |
| 1 | 39 |
| 2 | 61 |
| 3.5 | 86 |
| 5 | 94 |
| 7 | 100 |

Accelerated chemical stability tests at 55° C., in a light chamber and at 37° C./85% R.H., both in amber glass and polyethylene bottles with a silica plug showed the capsules to have acceptable stability.

The in vitro test was repeated utilizing the U.S.P. XIX Dissolution Test in Simulated Gastric Fluid at 100 RPM. The results of this test are given in Table II.

TABLE II

| Percent of Formulation Dissolved | |
|---|---|
| Time (hours) | % Dissolved, Range, S.D. |
| 0 | 0 |

TABLE II-continued

Percent of Formulation Dissolved

| Time (hours) | % Dissolved, Range, S.D. |
| --- | --- |
| 1 | 33 28-36 ± 1.9 |
| 4 | 69 62-75 ± 3.1 |
| 12 | 97 86-109 ± 4.3 |

Samples of capsules stored for 1 month at 37° C., 85% RH in amber glass and polyethylene, for 6 months in polyethylene at 37° C. and for 32 months at 25° C. in amber glass and polyethylene demonstrated comparable results. Similar tests conducted with capsules containing formulations of substantially larger particle size demonstrated a significantly less favorable dissolution pattern and correspondingly less desirable blood levels.

The in vitro dissolution results, i.e. percent formulation dissolved and percent chlordiazepoxide release were found to correlate very well with blood levels for chlordiazepoxide established in in vivo determinations.

Samples of the above capsules were tested in vivo in man in comparison with three commercial capsules each containing 10 mg. chlordiazepoxide administered at 4 and 8 hours. The results are set forth in Table III.

TABLE III

| | Time of Plasma Level Maxima (hrs.) | Plasma Level Maxima (gamma/ml.) | Total area under Plasma Level Curve |
| --- | --- | --- | --- |
| Sustained Release Capsule-30 mg. | | | |
| Mean | 9.6 | 1.06 | 27.2 |
| Range | (4-15) | (0.64-1.87) | (20.2-34.0) |
| No. of subjects | 6 | 6 | 6 |
| Commercial 10 mg. Capsules at 0.4 and 8 hours | | | |
| Mean | 9.4 | 1.04 | 24.5 |
| Range | (5.5-15) | (0.64-1.73) | (10.1-60.6) |
| No. of subjects | 17 | 17 | 17 |

It is evident from the above data that the sustained release capsules match very well with the regimen of single dose capsules.

EXAMPLE 2

In the same manner as Example 1, No. 2 capsules were filled with the following formulation.

| Ingredient | Mg/capsule |
| --- | --- |
| Diazepam | 15.3 |
| Hydroxypropylmethylcellulose, 4000 cps | 119.7 |
| Lactose, Anhydrous | 105.0 |
| Talc | 30.0 |
| Magnesium Stearate | 5.0 |
| Total | 275.0 |

These capsules demonstrated in vitro and in vivo results comparable to those realized with the capsules of Example 1.

EXAMPLE 3

Antianemic sustained release capsules were prepared as follows:

| Ingredient | mg/capsule |
| --- | --- |
| Ferrous Fumarate | 150 |
| Hydroxypropylmethylcellulose, 4000 cps | 100 |
| Lactose-DTG | 100 |
| Talc | 40 |
| Magnesium Stearate | 10 |
| Total | 400 |

The ferrous fumarate, hydroxypropylmethylcellulose and lactose were homogeneously mixed and passed through a Fitzpatrick Comminuting Machine with No. 0 plate, medium speed, knives forward. The talc and magnesium stearate were mixed with an aliquot of the initial mixture, screened through a 60 mesh screen and then added to the remainder of the initial powder mixture. The formulation was then mixed for an additional 15 minutes and filled into No. 1 capsules.

The dissolution rate of the capsules was determined in gastric fluid by modified NF method utilizing rotating bottles at 40 rpm. The results are set forth in Table IV.

TABLE IV

| Percent of Active Ingredient Released | |
| --- | --- |
| Time (hours) | Gastric Fluid (pH 1.2) |
| 0 | 0 |
| 1 | 45 |
| 2 | 85.7 |
| 3 | 98.6 |

The capsules remained buoyant throughout the test. The release of ferrous fumarate from capsules tested in pH change medium was very poor due to the low solubility of ferrous fumarate in relatively higher pH media. Such test results represent the effect of ferrous fumarate in conventional sustained release formulations which are not retained in the stomach.

EXAMPLE 4

Sustained release antacid capsules were prepared as follows:

| Ingredient | mg/capsule |
| --- | --- |
| FMA-11* | 254.7 |
| Magnesium Oxide, Light | 127.0 |
| Lactose, hydrous | 20.3 |
| Hydroxypropylmethylcellulose, 4000 cps | 63.0 |
| Gum Karaya, Stein Hall | 31.0 |
| Talc, tablet grade | 24.0 |
| Magnesium Stearate | 5.0 |
| Total | 525.0 |

*Aluminum Hydroxide-Magnesium carbonate co-precipitate - Reheis Co., Berkley Heights, New Jersey.

The FMA-11, light magnesium oxide, lactose and magnesium stearate were blended in a suitable mixer for 10 minutes and then passed through a Fitzpatrick Comminuting Maching using a No. 1 plate at medium speed, knives forward. The mixture was then slugged on a suitable press using ⅞ inch F.F. punch and the slugs milled on a Fitzpatrick Comminuting Machine at medium speed using a No. 1 plate, knives forward. The resulting granules were thoroughly mixed with the remaining ingredients and filled into No. 0 capsules utilizing conventional capsule filling equipment.

As the Federal Register does not give a specific method for testing a sustained release antacid preparation, the capsules were tested by the following method. A capsule is placed in 300 ml. of 0.1N hydrochloric acid in a stoppered flask rotated at 40 rpm. A 50 ml. sample is withdrawn at a specified time and titrated with 0.1N NaOH to pH 3.5 which is the neutralization point given in the Federal Register for acid neutralizing capacity. The amount of acid consumed was calculated from the sample. The results are given in Table V. The capsules remained floating throughout the test.

TABLE V

| Time | Antacid Release |
| --- | --- |
| 1st hour | 42.1% |
| 2nd hour | 96.7% |
| 3rd hour | 104% |

EXAMPLE 5

Sustained release aspirin capsules were prepared as follows:

| Ingredient | mg./capsule |
| --- | --- |
| Acetylsalicylic Acid, Micronized | 400 |
| Dicalcium Phosphate, anhydrous | 20 |
| Hydroxypropylcellulose HF | 40 |
| Tragacanth | 100 |
| Total | 560 |

All ingredients except tragacanth were thoroughly mixed and passed through a Fitzpatrick Comminuting Machine using a No. 00 plate, knives forward. The mixture was granulated with anhydrous ethanol, dried and milled. The tragacanth was then blended with the mixture and the whole filled into No. 0 capsules. The capsules were found to remain buoyant in the gastric fluid.

EXAMPLE 6

Sustained release capsules containing riboflavin prepared as follows:

| Ingredient | mg./capsule |
| --- | --- |
| Riboflavin, Type S* | 15 |
| Hydroxypropylmethylcellulose, 4000 cps | 110 |
| Lactose | 120 |
| Talc | 30 |
| Magnesium Stearate | 5 |
| Total | 280 |

*A type of riboflavin characterized by being less soluble and more crystalline than riboflavin phosphate.

All ingredients were thoroughly mixed and filled into No. 2 gelatin capsules. The release rate in gastric fluid was determined by the modified NF method at 40 r.p.m. The results are set forth in Table VI.

Table VI

| Time (hours) | % Active Ingredient Released |
| --- | --- |
| ½ | 34 |
| 1 | 45.3 |
| 2 | 62.6 |
| 3½ | 84.7 |
| 5 | 92.6 |

The capsules remained floating throughout the experiment.

EXAMPLE 7

Sustained release capsules containing riboflavin were prepared as follows:

| Ingredient | mg./capsule |
| --- | --- |
| Riboflavin, Type S | 15 |
| Guar Gum A-40F | 100 |
| Mannitol Powder, USP | 75 |
| Corn Starch | 60 |
| Tragacanth T300 | 30 |
| Total | 280 |

All ingredients except the tragacanth were combined and mixed in a suitable mixer. The resulting mixture was granulated with a mixture of equal parts of water and ethyl alcohol. The wet granulation was passed through a Fitzpatrick Comminuting Machine using a No. 3 plate, knives forward. The granulation was then dried at 110° F. and again passed through the Fitzpatrick Comminuting Machine using a No. 0 plate, knives forward. The tragacanth was added dry to the granulation, the whole was thoroughly mixed and filled into No. 2 gelatin capsules. The release rate of the capsules was determined by the modified NF method at 40 r.p.m. The results are set forth in Table VII.

Table VII

| Time (hours) | % Active Ingredient Released |
| --- | --- |
| ½ | 54.5 |
| 1 | 59.5 |
| 2 | 65.6 |
| 3½ | 78.5 |
| 5 | 88.8 |

The capsules remained floating throughout the experiment.

We claim:

1. A sustained release pharmaceutical capsule containing benzodiazepine selected from the group consisting of chloriazepoxide and diazepam in a formulation hydrodynamically balanced so that, upon contact with gastric fluid, said formulation acquires and maintains a bulk density of less than 1 thereby being buoyant in said fluid and remaining buoyant in the gastric fluid of the stomach until substantially all of said benzodiazepine contained therein has been released, said formulation comprising a finely particulate, homogeneous mixture of said benzodiazepine; from about 5% by weight to about 60% by weight of therapeutically inert, pharmaceutically acceptable adjunct materials, from 0% by weight to about 60% by weight of a fatty material having a specific gravity of less than one and from about 20% by weight to about 75% by weight of one or a mixture of hydrocolloids selected from the group consisting of methyl cellulose, hydroxypropylcellulose, hydroxypropylmethylcellulose, hydroxymethylcellulose and sodium-carboxymethylcellulose to provide, upon contact with gastric fluid, a water-impermeable barrier on the surface of said formulation.

2. The sustained release capsule according to claim 1 wherein said hydrocolloid is hydroxypropylmethylcellulose.

3. The sustained release capsule according to claim 1 wherein said benzodiazepine is chlordiazepoxide.

4. The sustained release capsule according to claim 1 wherein said benzodiazepine is diazepam.

* * * * *